United States Patent [19]

Durant et al.

[11] 4,083,988
[45] Apr. 11, 1978

[54] PHARMACOLOGICALLY ACTIVE COMPOUNDS

[75] Inventors: Graham John Durant, Welwyn Garden City; John Colin Emmett, Codicote; Charon Robin Ganellin, Welwyn Garden City, all of England

[73] Assignee: Smith Kline & French Laboratories Limited, Welwyn Garden City, England

[21] Appl. No.: 726,356

[22] Filed: Sep. 24, 1976

Related U.S. Application Data

[62] Division of Ser. No. 560,909, Mar. 21, 1975, Pat. No. 4,000,296, which is a division of Ser. No. 384,992, Aug. 2, 1973, abandoned.

[30] Foreign Application Priority Data

Sep. 5, 1972 United Kingdom ............... 41161/72

[51] Int. Cl.² ................. C07D 233/64; A61K 31/415
[52] U.S. Cl. ............................... 424/273 R; 548/337; 548/342; 424/273 P

[58] Field of Search ......... 260/309; 424/273; 548/337, 342

[56] References Cited

U.S. PATENT DOCUMENTS

| 3,734,924 | 5/1973 | Black et al. | 260/309 |
|-----------|--------|--------------|---------|
| 3,736,331 | 5/1973 | Black et al. | 260/309 |
| 3,808,336 | 4/1974 | Durant et al. | 424/273 |
| 3,950,333 | 4/1976 | Durant et al. | 260/309 |
| 4,000,296 | 12/1976 | Durant et al. | 260/309 |
| 4,000,302 | 12/1976 | Black et al. | 424/273 |

FOREIGN PATENT DOCUMENTS

| 779,775 | 8/1972 | Belgium. | |
|---------|--------|----------|---|
| 2,053,175 | 8/1971 | Germany | 260/309 |
| 2,211,454 | 10/1972 | Germany | 260/309 |

*Primary Examiner*—Natalie Trousof
*Attorney, Agent, or Firm*—Joan S. Keps; Richard D. Foggio; William H. Edgerton

[57] ABSTRACT

The compounds are guanidines, for example N-benzenesulphonyl-N'-[2-((4-methyl-5-imidazolyl)-methylthio)ethyl]guanidine, which are inhibitors of histamine activity.

7 Claims, No Drawings

PHARMACOLOGICALLY ACTIVE COMPOUNDS

This is a division of application Ser. No. 560,909 filed Mar. 21, 1975, now U.S. Pat. No. 4,000,296, which is a division of Ser. No. 384,992 filed Aug. 2, 1973 now abandoned.

This invention relates to pharmacologically active compounds, in particular to pharmacologically active guanidines, to processes of preparing these compounds and the pharmaceutical compositions and methods of inhibiting H-2 histamine receptors with these compounds. The compounds of the invention can exist as the addition salts but, for convenience, reference will be made throughout this specification to the parent compounds.

It has long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designed as H-1. A further group of substances has recently been described by Black et. al (Nature 1972, 236, 385) which are distinguished by the fact that they act at histamine receptors other than the H-1 receptor and these other receptors have been designed as H-2 receptors. This latter group of substances, to certain of which the present invention relates, are thus of utility in inhibiting certain actions of histamine which are not inhibited by the above-mentioned "antihistamines". The substances of this invention may also be of utility as inhibitors of certain actions of gastrin.

Throughout the present specification and claims, by the term "lower alkyl" we mean an alkyl group containing from 1 to 4 carbon atoms.

The guanidines with which the present invention is concerned may be represented by the following general formula:

FORMULA I

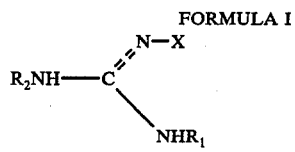

wherein $R_1$ is hydrogen or lower alkyl such as methyl; $R_2$ is a grouping of the structure shown in Formula II:

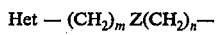

FORMULA II wherein Het is a nitrogen containing 5 or 6 membered heterocylic ring such as imidazole, pyridine, thiazole, isothiazole, oxazole, isoxazole, pyrazole, triazole, thiadiazole, pyrimidine, pyrazine, or pyridazine which is optionally substituted by lower alkyl, trifluoromethyl, hydroxyl, halogen or amino; Z is sulphur, oxygen, NH or a methylene group; $m$ is 0, 1 or 2 and $n$ is 2 or 3 the sum of $m$ and $n$ being from 2 to 4; X is $COR_3$, $CSR_3SO_2R_4$, $N=CHR_5$ or, when Z is methylene, nitro; $R_3$ is lower alkyl, lower alkoxy or amino; $R_4$ is lower alkyl, trifluoromethyl, amino or substituted or unsubstituted aryl, such as phenyl optionally substituted by halogen, lower alkyl or amino; and $R_5$ is substituted or unsubstituted aryl, such as phenyl or pharmaceutically acceptable acid addition salts thereof.

It will be understood that the structure illustrated in Formula I is only one of several representations and that other tautomeric forms are also covered by the present invention.

In a preferred group of compounds $R_1$ is methyl, $R_2$ is preferably Het — $CH_2S(CH_2)_2$ and is particularly preferably such that Het is an imidazolyl, thiazolyl, isothiazolyl or pyridyl ring, which ring is optionally substituted by methyl, hydroxyl, halogen or amino. Useful compounds are also obtained when X is phenylsulphonyl, aminosulphonyl or aminocarbonyl.

The compounds of the present invention may be produced from an amine of the formula $R_2NH_2$, wherein $R_2$ has the same significance as in Formula I by reaction thereof with a compound of Formula III.

FORMULA III

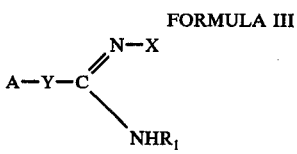

wherein $R_1$ and X have the same significance as in Formula I; Y is sulphur or oxygen; and A is lower alkyl e.g., methyl.

The production of the starting material of formula $R_2NH_2$ is described in our British Specification No. 1305547 and in our copending British applications Nos. 6352/71 and 34334/71.

Alternatively, reaction of the amine of formula $R_2NH_2$ with a compound of Formula IV:

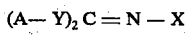

FORMULA IV wherein A, Y and X have the same significance as in Formula III results in the production of an intermediate compound of the following Formula V:

FORMULA V

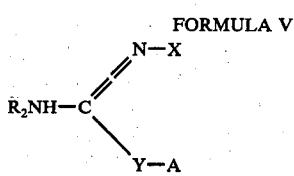

wherein A, Y, X and $R_2$ have the above significance. Reaction of this intermediate with $R_1NH_2$ wherein $R_1$ is hydrogen or lower alkyl yields the required compound of Formula I. This reaction scheme is particularly suitable for the production of those compounds wherein X is $SO_2R_4$. The compound of Formula IV wherein Y is sulphur is preferred and may be produced by the reaction of an aminosulphonyl compound of the formula $R_3SO_2NH_2$ under alkaline conditions with carbon disulphide and an alkyl halide of formula $R_1Hal$ wherein $R_1$ is lower alkyl and Hal is a halogen such as iodine.

Certain specific methods may also be used for the production of some particular compounds of Formula I. For example to produce those compounds wherein X is aminosulphonyl a guanidine of Formula VI:

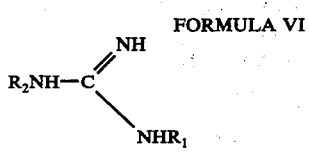

FORMULA VI wherein $R_1$ and $R_2$ have the same significance as in Formula I may be reacted with a diaminosulphonyl compound of Formula VII.

$$W{=}N.SO_2NH_2 \qquad \text{FORMULA VII}$$

wherein W is derived from a secondary amine of Formula W=NH e.g., piperidine.

A further specific method which may be used to produce those compounds of Formula I wherein X is aminocarbonyl involves mild acid hydrolysis e.g., with dilute hydrochloric acid at from 20° to 50° C of a cyanoguanidine compound of Formula VIII.

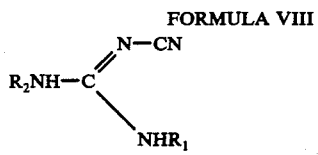

FORMULA VIII wherein $R_1$ and $R_2$ have the same significance as in Formula I. The compounds of Formula I wherein X is aminothiocarbonyl may also be prepared from the cyanoguanidine of Formula VIII by reaction thereof with hydrogen sulphide in a solvent such as pyridine and in the presence of a strong base such as triethylamine.

As stated above, the compounds represented by Formula I have been found to have pharmacological activity in the animal body as antagonists to certain actions of histamine which are not blocked by "antihistamines" such as mepyramine. For example, they have been found to inhibit selectively the histamine-stimulated secretion of gastric acid from the perfused stomachs of rats anaesthetised with urethane at doses of from 1 to 256 micromoles per kilogram intravenously.

Similarly, the action of these compounds may, in many cases, be demonstrated by their antagonism to the effects of histamine on other tissues which, according to the above-mentioned paper of Black et. al., are H-2 receptors. Examples of such tissues are perfused isolated guinea-pig heart, isolated guinea-pig right atrium and isolated rat uterus. The compounds of the invention have also been found to inhibit the secretion of gastric acid stimulated by pentagastrin or by food.

The level of activity found for the compounds of the present invention is illustrated by the effective dose range in the anaesthetised rat, as mentioned above of from 1 to 256 micromoles per kilogram, given intravenously. Many of the compounds of the present invention produce a 50% inhibition in this test at a dose of from 3 to 15 micromoles per kologram.

Pharmaceutical compositions comprising a pharmaceutical carrier and a compound of Formula I or a pharmaceutically acceptable acid addition salt thereof and methods of inhibiting the H-2 histamine receptors which comprises administering to an animal a compound of Formula I or a pharmaceutically acceptable acid addition salt thereof are also objects of this invention.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus if a solid carrier is used, the preparation can be tableted, placed in a hard gelatin capsule in powder or pellet form, or in the form of a troche or lozenge. The amount of solid carrier will vary widely but preferably will be from about 25 mg. to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg. to about 250 mg., most preferably from about 100 mg. to about 200 mg.

The active ingredient will preferably be administered in equal doses one to three times per day. The daily dosage regimen will preferably be from about 150 mg. to about 750 mg., most preferably from about 300 mg. to about 600 mg.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, picric and maleic acids.

Other pharmacologically active compounds may in certain cases be included in the composition. Advantageously the compositions will be made up in a dosage unit form appropriate to the desired mode of administration, for example as a tablet, capsule, injectable solution or as a cream for topical administration.

The invention is illustrated but in no way limited by the following examples:

EXAMPLE 1

N-[3-(4-Imidazolyl)propyl]-N'-nitroguanidine

A solution of 4(5)-(3-aminopropyl)imidazole (2.7 g.) and S-methyl-N-nitroisothiourea (2.9 g.) in methanol (50 ml.) was heated at 50°–65° for 4–5 hours. Concentration, followed by recrystallisation of the residue from methanol yielded N-[3-(4-imidazolyl)propyl]-N'-nitroguanidine, m.p. 156°–158°.

(Found: C, 39.7; H, 5.8; N, 39.4. $C_7H_{12}N_6O_2$ requires: C, 39.6; H, 5.7; N, 39.6)

EXAMPLE 2

N-Benzenesulphonyl-N'-[2-((4-methyl-5-imidazolyl)-methylthio)ethyl] guanidine A solution of 4-methyl-5-((2-aminoethyl)thiomethyl)imidazole (5.93g.) and N-benzenesulphonyl-S-methylisothiourea (8.0g.) in acetonitrile (100 ml.) was heated under reflux for 24 hours. Concentration, followed by chromatographic purification on a column of silica gel with benzene - methanol (10:1) and recrystallisation from aqueous ethanol and then acetonitrile afforded N-benzenesulphonyl-N'-[2-((4-methyl-5-imidazolyl)methylthio)ethyl]guanidine (2.5 g.) m.p. 149°–150°.

(Found: C, 47.8; H, 5.6; N, 19.9; S, 18.1. $C_{14}H_{19}N_5O_2S_2$ requires: C, 47.6; H, 5.4; N, 19.8; S, 18.1.)

EXAMPLE 3

N-Methyl-N'-[2-((4-methyl-5-imidazolyl)methylthio)ethyl-N"-trifluoromethanesulphonyl guanidine (a) A mixture of trifluoromethylsulphonamide (4.2 g.) and bis-S-methylthio-N-methylformimine, (7.6 g.) was heated at 120° for 4 hours. Cooling, followed by the addition of hexane afforded N, S-dimethyl-N'-trifluoromethanesulphonylisothiourea (5.0g.) m.p. 88°–89°.

(Found: C, 20.3; H, 3.0; N, 11.9; S, 27.2. $C_4H_7F_3N_2O_2S_2$ requires: C, 20.3; H, 3.0; N, 11.9; S, 27.2)

(b) A solution of 4-methyl-5-((2-aminoethyl)thiomethyl)imidazole (3.54 g.) and N, S-dimethyl-N'-trifluoromethanesulphonylisothiourea (4.90 g.) in ethanol (50 ml.) was heated under reflux for 24 hours. Concentration, followed by chromatographic purification on a column of silica gel with ethyl acetate-ethanol (4:1) as eluant yielded N-methyl-N'-[2-((4-methyl-5-imidazolyl)methylthio)ethyl]-N"-trifluoromethanesulphonylguanidine as a glass (2.8 g.)

(Found: C, 33.5; H, 4.7; S, 17.5. $C_{10}H_{16}F_3N_5O_2S_2$ requires: C, 33.4; H, 4.5; S, 17.8.)

EXAMPLE 4

N-(4-Chlorobenzenesulphonyl)-N'-methyl-N"-[2-((4-methyl-5-imidazolyl)methylthio)ethyl]guanidine (a) A mixture of 4-chlorobenzenesulphonamide (6.0 g.) and bis-S-methylthio-N-methylformimine (8.5g.)was heated at 120°–125° for 4 hours to give N-(4-chlorobenzenesulphonyl)-N',S-dimethylisothiourea (5.8 g.), m.p. 121°–123° (from ethanol-hexane).

(Found: C, 38.5; H, 4.1; N, 9.9; Cl, 12.7; S, 22.8. $C_9H_{11}Cl\,N_2O_2S_2$ requires: C, 38.8; H, 4.0; N, 10.1; Cl, 12.7; S, 23.0)

(b) A solution of 4-methyl-5-((2-aminoethyl)thiomethyl)imidazole (3.33 g.) and N-(4-chlorobenzenesulphonyl)-N',S-dimethylisothiourea (5.40 g.) in acetonitrile was heated under reflux for 24 hours. Concentration, followed by recrystallisation from aqueous ethanol afforded N-(4-chlorobenzenesulphonyl)-N'-methyl-N"-[2-((4-methyl-5-imidazolyl)methylthio)ethyl]guanidine (4.6 g.), m.p. 153°–154°.

(Found: C, 44.9; H, 5.1; N, 17.1; Cl, 8.8; S, 15.7 $C_{15}H_{20}N_5O_2S_2$ requires: C, 44.8; H, 5.0; N, 17.4; Cl, 8.8; S, 16.0.

EXAMPLE 5

N-(3,4-Dichlorobenzenesulphonyl)-N'-methyl-N"-[2-((4-methyl-5-imidazolyl)methylthio)ethyl]guanidine (a) A mixture of 3,4-dichlorobenzenesulphonamide (6.5 g.) and bis-S-methylthio-N-methylformimine (8.0 g.) was heated at 120° for 4 hours to give N-(3,4-dichlorobenzenesulphonyl)-N',S-dimethylisothiourea (7.3 g.) m.p. 158°–159° (from methanol).

(Found: C, 34.4; H, 3.1; N, 8.9; Cl, 22.9; S, 20.4. $C_9H_{10}Cl_2N_2O_2S_2$ requires: C, 34.5; H, 3.2; N, 8.9; Cl, 22.6; S, 20.2)

(b) A solution of 4-methyl-5-((2-aminoethyl)thiomethyl)imidazole (3.49 g.) and N-(3,4-dichlorobenzenesulphonyl)-N', S-dimethylisothiourea (6.20 g.) in acetonitrile (250 ml.) was heated under reflux for 48 hours. Concentration, followed by chromatographic purification on a column of alumina with sequential elution by benzene-ethylacetate (1:4) and benzene-ethanol (1:4) afforded N-(3,4-dichlorobenzenesulphonyl)-N'-methyl-N"-[2-((4-methyl-5-imidazolyl)methylthio)ethyl] guanidine as a glass (1.7 g.)

(Found: C, 41.7; H, 4.8; N, 15.9; Cl, 16.3; S, 14.4 $C_{15}H_{19}N_5Cl_2O_2S_2$ requires: C, 41.3; H, 4.4; N, 16.1; Cl, 16.3; S, 14.7.)

EXAMPLE 6

N-Benzenesulphonyl-N'-methyl-N"-[2-((4-methyl-5-imidazolyl)methylthio)ethyl]guanidine A solution of N-benzenesulphonyliminodithiocarbonic acid dimethyl ester (13.0 g.) and 4-methyl-5-((2-aminoethyl)thiomethyl)imidazole (8.5 g.) in ethanol (100 ml.) was stirred at room temperature for 4 hours. Excess ethanolic methylamine was added and stirring was continued for 2 hours at room temperature. Following concentration, the residue was dissolved in ethanol-ether (1:1) and chilled affording N-benzenesulphonyl-N'-methyl-N"-[2-((4-methyl-5-imidazolyl)methylthio) ethyl]guanidine (15.0 g.), m.p. 156.5° – 157.5° (from water)

(Found: C, 49.0; H, 5.8; N, 19.0; S, 17.3. $C_{15}H_{21}N_5O_2S_2$ requires: C, 49.0; H, 5.8; N, 19.1; S, 17.5.

EXAMPLE 7

N-Methylanesulphonyl-N'-methyl-N"-[2-((4-methyl-5-imidazolyl)methylthio) ethyl]guanidine A solution of N-methanesulphonylimidithiocarbonic acid dimethyl ester (10.0 g.) and 4-methyl-5-((2-aminoethyl)thiomethyl)imidazole (8.5 g.) in ethanol (100 ml.) was stirred at room temperature for 3 hours. Excess ethanolic methylamine was added and stirring continued for 3 hours at room temperature. Concentration and trituration with ice-water afforded H-methanesulphonyl-N'-methyl-N"-[2-((4-methyl-5-imidazolyl)methylthio)ethyl]guanidine (12.7 g.), m.p. 133°–134° (from water)

(Found: C, 39.2; H, 6.4; N, 22.6; S, 20.7 $C_{10}H_{19}N_5O_2S_2$ requires: C, 39.3; H, 6.3; N, 22.9; S, 21.0.)

EXAMPLE 8

N-Ethanesulphonyl-N'-methyl-N"-[2-((4-methyl-5-imidazolyl)methylthio) ethyl]guanidine To a solution of ethanesulphonamide (12.0 g.) in dimethylformamide (75 ml.) at 4°, was added a solution of sodium hydroxide (4.45 g.) in water (6 ml.) and carbon disulphide (3.6 ml.) After stirring for 10 minutes at 5° sodium hyroxide (2.2 g.) in water (3 ml.) and carbon disulphate (1.5 ml) was added and after a further 10 minutes similar quantities of sodium hydroxide and carbon disulphide were again added. After stirring for 10 minutes at 5°, methyl iodide (42.6 g.) was added without external cooling and stirring was continued for 2 hours and the reaction mixture added to water (750 ml.) Extraction with ether and concentration yielded crude N-ethanesulphonyliminodithiocarbonic acid dimethyl ester (6. 4 g.) This was reacted directly with 4-methyl-5-((2-aminoethyl)thiomethyl)imidazole (5.0 g.) and methylamine in ethanol by the method described in Example 7. The product was chromatographed on a column of silica gel with ethyl acetate-ethanol (2:1) as eluant to yield N-ethanesulphonyl-N'-methyl-N"-[2-((4-methyl-5-imidazolyl)methylthio)ethyl]guanidine as a glass (4.0 g.)

(Found: C, 41.2; H, 7.4; N, 21.0; S, 19.1. $C_{11}H_{21}N_5O_2S_{2(+3\% \ C_2H_5OH)}$ requires: S, 41.7; H, 7.5; N, 21.3; S, 19.5.

EXAMPLE 9

N-Methyl-N'-[2-((4-methyl-5-imidazolyl)methylthio)ethyl]-N"-n-propanesulphonylguanidine (a) Reaction of n-propanesulphonamide with sodium hydroxide, carbon disulphide and methyliodide by the method described in Example 8 afforded N-n-propanesulphonyliminodithiocarbonic acid dimethyl ester, m.p. 73°–74° (from ethanol-hexane).

(Found: C, 31.7; H, 5.7; N, 6.2; S, 42.0. $C_6H_{13}NO_2S_3$ requires: C, 31.7; H, 5.8; N, 6.2; S, 42.3)

(b) The reaction of N-n-propanesulphonyliminodithiocarbonic acid (4.7 g.) dimethyl ester with 4-methyl-5-((2-aminoethyl)thiomethyl)imidazole (3.5 g.) and methylamine by the method described in Example 7 followed by chromatographic purification on a column of silica gel with ethyl acetate-ethanol (4:1) as eluant afforded N-methyl-N'-[2-((4-methyl-5-imidazolyl)methylthio)ethyl]-N"-n-propanesulphonylguanidine as a glass (5.0 g.).

(Found: N, 20.1; S, 18.4; $C_{12}H_{23}N_5O_2S_2$ (+5% $C_2H_5OH$) requires: N, 20.0; S, 18.3.)

EXAMPLE 10

N-Methyl-N'-[2-((4-methyl-5-imidazolyl)methylthio)ethyl]-N"-p-toluenesulphonylguanidine The reaction of N-p-toluenesulphonyliminodithiocarbonic acid dimethyl ester (10.0 g.) with 4-methyl-5-((2-aminoethyl)thiomethyl)imidazole (6.2 g.) and methylamine by the method described in Example 6, afforded N-methyl-N'-[2-((4-methyl-5-imidazolyl)methylthio)ethyl]-N"-p-toluenesulphonylguanidine (5.5 g.), m.p. 137.5°–138.5° (from ethanol-ether)

(Found: C, 50.4; H, 6.2; N, 18.3; S, 17.0 $C_{16}H_{23}N_5O_2S_2$ requires: C, 50.4; H, 6.1; N, 18.4; S, 16.8)

EXAMPLE 11

N-[2-((4-Methyl-5-imidazolyl)methylthio)ethyl]-N'-sulphamylguanidine (a) A solution of 4-methyl-5-((2-aminoethyl)thiomethyl)imidazole (19.0 g.) and S-methylisothiourea sulphate (15.1 g.) in water (100 ml.) was heated under reflux for 3 hours. Concentration, acidification with sulphuric acid and dilution with ethanol afforded 2-[(4-methyl-5-imidazolyl)methylthio)ethyl]guanidine sulphate (13.0 g.) m.p. 230°–235° (from aqueous methanol).

(b) The guanidine sulphate (10.0 g.) was added to a solution of sodium (1.53 g.) in ethanol (100 ml.) Filtration and concentration gave the guanidine base which was dissolved in dimethylsulphoxide (20 ml.) and added gradually to a solution of N-piperidylsulphamide (5.3 g.) in dimethylsulphoxide (10 ml.) The mixture was heated on the steam bath for 2 hours and concentrated under reduced pressure. The residue was chromatographed on a column of silica gel with ethylacetate-ethanol (3:2) as eluant yielding a product (2.38 g.) which was recrystallised from water and then methanolether to give N-[2-((4-methyl-5-imidazolyl)methylthio)ethyl]-N'-sulphamylguanidine, m.p. 130°–133°.

(Found: C, 32.5; H, 5.6; N, 28.3; S, 21.6. $C_8H_{16}N_6O_2S_2$ requires: C, 32.8; H, 5.8; N, 28.7; S, 21.9)

EXAMPLE 12

N-Methyl-N'-[2-((4-methyl-5-imidazolyl)methylthio)ethyl]-N"-sulphamylguanidine (a) A solution of N-cyano-N'-methyl-N"-[2-((4-methyl-5-imidazolyl)methylthio)ethyl]guanidine (2.0 g.) in hydrochloric acid (25 ml.) was heated on the steam bath for 2 hours. Concentration followed by recrystallisation of the product from ethanol-ether afforded N-methyl-N"-[2-((4-methyl-5-imidazolyl)methylthio)ethyl]guanidine dihydrochloride (1.44 g.) m.p. 204°–206°.

(Found: C, 35.8; H, 6.5; S, 10.8; Cl, 23.7. $C_9H_{17}N_5S.2$ HCl requires: C, 36.0; H, 6.4; S, 10.7; Cl, 23.6)

(b) The guanidine dihydrochloride (3.0 g.) was added to a solution of sodium (0.46 g.) in ethanol (50 ml.) and following warming with stirring for 0.5 hours, the mixture was cooled and filtered, N-Piperidylsulphamide (1.64 g.) was added to the filtrate which was heated under reflux for 24 hours. Following concentration the residue was chromatographed firstly on silica gel with ethyl acetate-ethanol (4:1) as eluant and then on alumina with a similar eluant, to yield N-methyl-N'-'-[2-((4-methyl-5-imidazolyl)methylthio)ethyl]-N" -sulphamylguanidine as a glass (1.05 g.)

(Found: C, 36.1; H, 6.1; N, 26.1; S, 19.8. $C_9H_{18}N_6O_2S_2$ (+3% $C_2H_5OH$) requires: C, 35.8; H, 6.1; N, 26.6; S, 20.3)

EXAMPLE 13

N-(4-Aminobenzenesulphonyl)-N'-methyl-N"-[2-(4-methyl-5-imidazolyl) methylthio)ethyl]guanidine (a) The reaction of 4-aminobenzenesulphonamide (17.2.g.) with sodium hydroxide, carbon disulphide and methyl iodide by the method described in Example 8, afforded N-(4-aminobenzenesulphonyl)iminodithiocarbonic acid dimethyl ester (9.4 g.), m.p. 202–204° (from ethanol).

(b) The reaction of N-(4-aminobenzenesulphonyl)iminodithiocarbonic acid dimethyl ester (8.9 g.) with 4-methyl-5-((2-aminoethyl)thiomethyl)imidazole (5.5 g.) and methylamine by the method described in Example 7, followed by chromatographic purification on a column of alumina with ethyl acetate ethanol (4:1) as eluant afforded (N-(4-aminobenzenesulphonyl)-N'-methyl-N"-[2-((4-methyl-5-imidazolyl)methylthio)ethyl]guanidine as a glass.

(Found: S, 16.7%. $C_{15}H_{22}N_6O_2S_2$ requires: S, 16.8%)

EXAMPLE 14

N-Acetyl-N'-[2-((4-methyl-5-imidazolyl)methylthio)ethyl]guanidine

N-Acetyl-S-methylisothiouronium iodide (5. 20 g.) was dissolved in acetonitrile (100 ml.), excess solid potassium carbonate added and the suspension stirred at room temperature for 0.5 hours. Following filtration, 4-methyl-5-((2-aminoethyl)thiomethyl)imidazole (3.42 g.) was added and stirring was continued at room temperature for 48 hours. The white solid formed during the reaction was collected and recrystallised from acetonitrile to give N-acetyl-N'-[2-((4-methyl-5-imidazolyl)methylthio)ethyl]guanidine, m.p. 163°–164°.

(Found: C, 47.0; H, 6.9; N, 27.4; S,12.4; $C_{10}H_{17}N_5SO$ requires: C, 47.0, H, 6.7; N, 27.4; S, 12.6)

EXAMPLE 15

N-Carbethoxy-N'-[2-((4-methyl-5-imidazolyl)methylthio)ethyl]guanidine

A solution of N-carbethoxy-O-methylisourea (1.46 g.) and 4-methyl-5-((2-aminoethyl)thiomethyl)imidazole (1.71 g.) in methanol (25 ml) was stirred at room temperature for 7 days. The white solid formed during the reaction was collected and recrystallised from methanol to give N-carbethoxy-N'-[2-((4-methyl-5-imidazolyl)methylthio)ethyl]guanidine m.p. 196°–197°.

(Found: C, 46.5; H, 6.9; N, 24.8; S, 11.5. $C_{11}H_{19}N_5O_2S$ requires: C, 46.3; H, 6.7; N, 24.5; S, 11.2)

EXAMPLE 16

N-Carbamyl-N'-methyl-N''-[2-((4-methyl-5-imidazolyl)methylthio))ethyl]guanidine dihydrochloride A solution of N-cyano-N'-methyl-N''-[2-((4-methyl-5-imidazolyl)methylthio)ethyl]guanidine (1.25 g.) in N hydrochloric acid (15 ml.) was kept at room temperature for 60 hours, and then heated at 40°–45° for 20 hours. Following concentration and basification with sodium ethoxide in ethanol, the product was chromatographed on silica gel with isopropyl alcohol as eluant. Acidification with ethanolic hydrogen chloride and final recrystallisation from isopropyl alcohol afforded N-carbamyl-N'-methyl-N''-[2-((4-methyl-5-imidazolyl)methylthio)ethyl]guanidine dihydrochloride (0.60 g.) m.p. 186°–187°.

(Found: C, 35.1; H, 6.1; N, 23.9; Cl, 20.6. $C_{10}H_{18}N_6OS$. 2 HCl requires: C, 35.0; H, 5.9; N, 24.5; Cl, 20.7.

EXAMPLE 17

N-Methyl-N'-[2-((4-methyl-5-imidazolyl)methylthio)ethyl]-N''-thiocarbamylguanidine Gaseous hydrogen sulphide was passed through a solution of N-cyano-N'-methyl-N''-[2-((4-methyl-5-imidazolyl)methylthio)ethyl]guanidine (5.0 g.) in pyridine (45 ml.) containing triethylamine (9 ml.) at room temperature for 24 hours and at 50° for a similar period. Concentration, followed by chromatographic purification on a column of silica gel with ethylacetate-isopropyl alcohol (5:1) as eluant and acidification with ethanolic hydrogen chloride afforded N-methyl-N'-[2-((4-methyl-5-imidazolyl)methylthio)ethyl]-N''-thiocarbamylguanidine (2.4 g.), m.p. 170°–171° (from isopropyl alcohol)

(Found: C, 33.4; H, 5.7; N, 23.0; S, 17.6; Cl, 19.5. $C_{10}H_{18}N_6S_2.2HCl$ requires: C, 33.4; H, 5.6; N, 23.4; S, 17.9; Cl, 19.7.

EXAMPLE 18

N-Benzylideneamino-N'-methyl-N''-[2-((4-methyl-5-imidazolyl)methylthio)ethyl]guanidine A solution of benzaldehyde-4-methylthiosemicarbazone (3.9 g.) and methyliodide (11. 2.g.) in absolute ethanol (40 ml.) was heated under reflux for 16 hours. Concentration and recrystallisation from ethanol afforded the S-methylisothiouronium iodide (5.3 g.) m.p. 194°–196°, which was basified with aqueous sodium carbonate and extracted with ethyl acetate to afford the base (2.5 g.) This was dissolved in ethanol containing 4-methyl-5-((2-aminoethyl)thiomethyl)imidazole (2.0 g.)and the solution heated under reflux for 3 days. Concentration followed by purification on a column of silica gel with ethanol as eluant afforded N-benzylideneamino-N''-[2-((4-methyl-5-imidazolyl)methylthio)ethyl]guanidine as a low melting solid.

(Found: C, 58.1; H, 7.0; S, 9.7; $C_{16}H_{22}N_6S$ requires: C, 58.2; H, 6.7; S, 9.7.

EXAMPLE 19

Sequential reaction of N-benzenesulphonyliminodithiocarbonic acid dimethyl ester according to a process similar to that described in Example 6 with any of the following substances:

(a) 4-bromo-5-[(2-aminoethyl)thiomethyl]imidazole
(b) 4-[4-aminobutyl]imidazole
(c) 2-[(2-aminoethyl)thiomethyl]thiazole
(d) 3-[(2-aminoethyl)thiomethyl]isothiazole
(e) 3-hydroxy-2[(2-aminoethyl)thiomethyl]pyridine
(f) 2-[(2-aminoethyl)thiomethyl]oxazole
(g) 3-[(2-aminoethyl)thiomethyl]isoxazole
(h) 2-[(2-aminoethyl)thiomethyl]pyrazine
(i) 3-[(2-aminoethyl)thiomethyl]pyridazine
(j) 3-[(2-aminoethyl)thiomethyl]pyrazole
(k) 3-[2-aminoethyl)thiomethyl]-1,2,4-triazole
(l) 5-amino-2-[(2-aminoethyl)thiomethyl]-1,3,4-thiadiazole
(m) 4-trifluoromethyl-5-[(2-aminoethyl)thiomethyl]-imidazole
(n) 2-[(2-aminoethyl)thiomethyl]pyrimidine
(o) 4-[(2-aminoethoxy)methyl]imidazole
(p) 4-methyl-5-[(3-aminopropyl)thiomethyl]imidazole
(q) 4-[(2-aminoethyl)aminoethyl]imidazole and then with exces methylamine results respectively in the production of the following compounds:

(a) N-benzenesulphonyl-N'-methyl-N''-[2-((4-bromo-5-imidazolyl) methylthio)ethyl]guanidine
(b) N-benzenesulphonyl-N'-methyl-N''-[4-(4-imidazolybutyl]guanidine
(c) N-benzenesulphonyl-N'-methyl-N''-[2-((2-thiazolyl)methylthio)ethyl] guanidine
N-benzenesulphonyl-N'-methyl-N''-[2-((3-isothiazolyl)methylthio) ethyl]guanidine
(e) benzenesulphonyl-N'-methyl-N''-[2-((3-hydroxy-2-pyridyl)methylthio) ethyl]guanidine
(f) N-benzenesulphonyl-N'-methyl-N''-[2-((2-oxazolyl)methylthio) ethyl]guanidine
(g) N-benzenesulphonyl-N'-methyl-N''-[2-((3-isoxazolyl)methylthio) ethyl]guanidine (h) N-benzenesulphonyl-N'-methyl-N''-[2-((2-pyrazinyl)methylthio) ethyl]guanidine
(i) N-benzenesulphonyl-N'-methyl-N''-[2-((3-pyridazyl)methylthio) ethyl]guanidine
(j) N-benzenesulphonyl-N'-methyl-N''-[2-((3-pyrazyl)methylthio)ethyl] guanidine
(k) N-benzenesulphonyl-N'-methyl-N''-[2-((3-1,2,4-triazolyl)methylthio) ethyl]guanidine
(l) N-benzenesulphonyl-N'-methyl-N''-[2-((5-amino-2-1,3,4-thiadiazolyl) methylthio)ethyl]guanidine
(m) N-benzenesulphonyl-N'-methyl-N''-[2-((4-trifluoromethyl-5-imidazolyl)methylthio)ethyl]guanidine
(n) N-benzenesulphonyl-N'-methyl-N''-[2-((2-pyrimidinyl)methylthio) ethyl]guanidine.
(o) N-benzenesulphonyl)-N'-methyl-N''-[2-((4-imidazolyl)methoxy) ethyl]guanidine
(p) N-benzenesulphonyl-N'-methyl-N''-[3-((4-methyl-5-imidazolyl) methylthio)propyl]guanidine.
(q) N-benzenesulphonyl-N'-methyl-N''-[2 -((4-imidazolyl)methylamino) ethyl]guanidine.

EXAMPLE 20

Sequential reaction of N-benzenesulphonyliminodithiocarbonic acid dimethyl ester according to a process similar to that described in Example 6 with either of the following compounds:

(a) 4-[(2-aminoethyl)thioethyl]imidazole
(b) 2-[(3-aminopropyl)thio]imidazole and then with excess methylamine results respectively in the production of the following compounds:

(a) N-benzenesulphonyl-N'-methyl-N''-[2-((4-imidazolyl)ethylthio)ethyl] guanidine.
(b) N-benzenesulphonyl-N'-methyl-N''-[3-((2-imidazolyl)thio)propyl] guanidine

EXAMPLE 21

Reaction of the amines set out in Example 19 with N-benzenesulphonyliminodithiocarbonic acid dimethyl ester as described therein and then with ethylamine or with butylamine resulted respectively in the corresponding compounds of Formula I wherein $R_1$ is ethyl or butyl.

EXAMPLE 22

| INGREDIENTS. | AMOUNTS |
|---|---|
| N-benzenesulphonyl-N'-methyl-N''-[2-((4-methyl-5-imidazolyl)-methylthio)ethyl]guanidine | 150 mg. |
| sucrose | 75 mg. |
| starch | 25 mg. |
| talc | 5 mg. |
| stearic acid | 2 mg. |

The ingredients are screened, mixed and filled into a hard gelatin capsule.

We claim:
1. A compound of the formula:

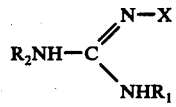

wherein $R_1$ is hydrogen or lower alkyl; $R_2$ is a grouping of the formula

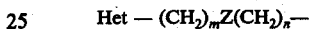

wherein Het is imidazole which is attacked at a ring carbon and which is optionally substituted by lower alkyl, trifluoromethyl or halogen; Z is sulphur, oxygen, NH or a methylene group; $m$ is 0, 1 or 2 and $n$ is 2 or 3, the sum of $m$ and $n$ being from 2 to 4; X is $COR_3$ or $CSR_3$; and $R_3$ is lower alkyl or lower alkoxy or a pharmaceutically acceptable acid addition salt thereof.

2. A compound according to claim 1 wherein X is $COR_3$; and $R_3$ has the same significance as in claim 1.

3. A compound according to claim 1 wherein $R_1$ is methyl.

4. A compound according to claim 1 wherein Z is sulphur, $m$ is 1 and $n$ is 2.

5. A compound according to claim 1 wherein Het is an imidazolyl ring which ring is optionally substituted by methyl or halogen.

6. A pharmaceutical composition to inhibit H-2 histamine receptors comprising in an effective amount to inhibit said receptors a compound according to claim 1 and a non-toxic pharmaceutically acceptable diluent or carrier.

7. A method of inhibiting H-2 histamine receptors which comprises administering to an animal in need of inhibition of said receptors in an effective amount to inhibit said receptors a compound of claim 1.

* * * * *